United States Patent [19]
Reichle

[11] Patent Number: 4,458,026
[45] Date of Patent: Jul. 3, 1984

[54] CATALYSTS FOR ALDOL CONDENSATIONS

[75] Inventor: Walter T. Reichle, Warren, N.J.

[73] Assignee: Union Carbide Corporation, Danbury, Conn.

[21] Appl. No.: 498,146

[22] Filed: May 25, 1983

Related U.S. Application Data

[62] Division of Ser. No. 384,212, Jun. 2, 1982.

[51] Int. Cl.$^3$ ............................................. B01J 21/16
[52] U.S. Cl. ........................................ 502/80; 502/85; 423/129; 423/165; 423/595; 423/637
[58] Field of Search ............... 252/463, 473; 502/80, 502/85; 423/129, 165, 595, 637

[56] References Cited

U.S. PATENT DOCUMENTS

| | | | |
|---|---|---|---|
| 3,796,792 | 3/1974 | Miyata et al. | 423/250 |
| 3,879,523 | 4/1975 | Miyata et al. | 423/250 |
| 3,879,525 | 4/1975 | Miyata et al. | 423/277 |
| 4,086,188 | 4/1978 | Reichle | 252/463 |
| 4,165,339 | 8/1979 | Reichle | 260/586 |

OTHER PUBLICATIONS

Physiochemical Properties and Structure of MgO–Al$_2$O$_3$, Miyata et al., Nippon Kagaku Zasshi, vol. 92, No. 6, pp. 514–519, (1971).
Applied Clay Mineralogy, Grim, R. E., McGraw-Hill Book Co., Inc., New York, 1962, pp. 1–3, 39 and 40.
S. Miyata et al., Nippon Kagaku Zasshi, vol. 29, No. 6, pp. 514–519, (1971).

*Primary Examiner*—Carl F. Dees
*Attorney, Agent, or Firm*—Bernard Francis Crowe

[57] ABSTRACT

Heat treated anionic clay mineral is an improved catalyst for the conversion of acetone to mesityl oxide and isophorone as well as for the aldol condensation of other carbonyl-containing compounds.

17 Claims, No Drawings

CATALYSTS FOR ALDOL CONDENSATIONS

This is a division of Ser. No. 384,212 filed June 2, 1982.

BACKGROUND OF THE INVENTION

This invention pertains to aldol condensations catalyzed by heat-treated synthetic anionic clay minerals and more particularly to the use of these catalysts for the conversion of acetone to mesityl oxide and isophorone.

The aldol condensation of active hydrogen-containing organic carbonyl compounds has found wide use in the chemical industry for the synthesis of a myriad of organic compounds. The earliest catalysts used for this condensation reaction were bases, such as, alkali metal hydroxides which have been used for the production of 2-ethylhexanediol-1, 3, 2-ethylhexanol-1, diacetone alcohol, isophorone, mesityl oxide, methylisoamyl ketone, methylisobutyl ketone and the like.

A variety of methods has been disclosed in the literature for converting, for example, acetone by aldol condensation into a wide spectrum of products particularly isophorone and mesityl oxide which are used in industrial solvents and as chemical intermediates for resins, dyes, intersecticides, and the like. By-products which arise from the general aldol condensation reaction wih acetone include diacetone alcohol, 4,4-dimethyl-hepta-2,6-dione, 4,6-dimethyl-hepta-3,5-diene-2-one, 3,5,5-trimethyl cyclohex-3-ene-one, mesitylene, 2,2,6,6-tetramethyl tetrahydropyran-4-one, xylitones, and isoxylitones, as well as various unidentified high boilers and tars. The specificity of the reaction must be controlled for commercial success in order to direct conversion of acetone to the desired end products.

Examples of prior catalysts used for conversion acetone to isophorone and mesityl oxide are: alkali metal hydroxides, such as, sodium, potassium, and lithium hydroxide; alkaline earth hydroxides, such as calcium, magnesium, strontium and barium hydroxide; calcium aluminate, calcium borate, potassium zincate, magnesium plumbate, barium aluminate, lithium plumbate, sodium borate, strontium stannate, potassium stannate, calcium borate, magnesium antimonate, sodium antimonate, calcium arsenate, sodium arsenate, potassium titanate, calcium zincate, magnesium aluminate, beryllium aluminate, cesium borate, rubidium arsonate, lithium phosphate, magnesium oxide, and the like.

In addition a recently discovered magnesium-aluminum hydroxide based catalyst has been described in U.S. Pat. No. 4,165,339 which affords efficiencies of about 80 percent (acetone to mesityl oxide and isophorone) at a conversion of about 15 to 18 percent per pass.

It is an object of this invention to provide an aldol condensation catalyst particularly for the conversion of acetone to mesityl oxide and isophorone having both enhanced efficiencies and conversions of acetone.

It is a further object of this invention to control the condensation of acetone to produce chiefly mesityl oxide and isophorone and in addition to limit the molar ratio of mesityl oxide: isophorone produced to a low value, preferably less than one, to conform to tne commercial demand for these two products.

It is still a further object of this invention to provide a catalyst for this aldol condensation of acetone having the following properties:
High and constant activity
Reproducible activity
Long catalyst life
Ability to be regenerated readily
Consistent in selective production of
mainly mesityl oxide and isophorone
Cheaper and available It is also an object of this invention to provide a catalyst and method for the aldol condensation of active hydrogen-containing organic carbonyl compounds in general.

SUMMARY OF THE INVENTION

An improved catalyst for aldol condensations of active hydrogen containing organic compounds has been developed. These materials are based on synthetic anionic clay minerals, which after appropriate heat activation, result in these superior catalysts.

These synthetic inorganic materials belong to the hydrotalcite-sjogrenite-pyroaurite and related mineral classes. Their ideal composition is represented by the generic formula:

$$M_m N_n (OH)_{2m+2n} A_a \cdot bH_2O$$

wherein
M is a divalent metal cation;
N is a trivalent metal cation;
A is a mono-, di- or trivalent anion which decomposes at about 300°–500° C. to hydroxyl ions;
m and n are integers such that m/n has values of 1 to about 6;
a is an integer with the provisos that when A is a monovalent anion $a=n$, when A is a divalent anion $a=\frac{1}{2}n$, and when A is a trivalent anion $a=\frac{1}{3}n$; and
b is an integer having values of 0 to 10.

These synthetic anionic clay minerals are converted to the actual catalysts for aldol condensations by heating them to a temperature of about 300° C. to about 600° C. whereby the anion moiety is decomposed to hydroxyl ion.

The structure of these materials is essentially that of brucite ($Mg(OH)_2$). In brucite the metal is in an octahedral environment of hydroxyls. These octahedra share edges and thereby form extended sheets. These sheets are stacked on top of each other much like sheets of paper. In the hydrotalcite, for example, the magnesium and aluminum are in these octahedra which generate the metal oxide sheets. Since each aluminum cation has one more positive charge than the magnesium cation, the sheets have gained one unit of positive change per aluminum ion. This is compensated for by suitable anions located interstitially. Additionally, there are some water molecules located between each metal ion sheet. These minerals can be prepared synthetically and this allows a variation of the $M^{+2}/N^{+3}$ ratio, a wide variation of the kind of anion as well as various other features which will be discussed below.

Heat treatment of these synthetic materials, which by themselves are only partly active, converts them into highly active catalysts. On heating to over 300° the interstitial water molecules and the decomposition product(s) of the anion are expelled and hydroxyl groups are converted to metal oxide and water. For hydrotalcite the stoichiometry is as follows:

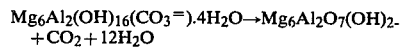

$$Mg_6Al_2(OH)_{16}(CO_3^=) \cdot 4H_2O \rightarrow Mg_6Al_2O_7(OH)_2 + CO_2 + 12H_2O$$

The volatile carbon dioxide and water escape and the residue is a very intimate mixture of metal oxides with approximately one hydroxide per $M^{+3}$ remaining on the oxide skeleton. Further consequences of this heating process are discussed below.

The general method for the preparation of the catalyst is illustrated by the preparation of Mg/Al/carbonate hydrotalcite which involves the addition of mixed magnesium/aluminum nitrates, sulphates or chlorides as an aqueous solution to a solution of a stoichiometric amount of sodium hydroxide and carbonate at about 25°-35° C. with vigorous stirring over about a several-hour period producing a slurry. This slurry is then heated for about 18 hours at about 50°-200° C. (preferably 60°-75° C.) in order to allow a limited amount of crystallization to take place. After filtering the solids, and thorough washing and drying, the dry solids are recovered.

This procedure is readily adaptable to variations in the Mg/Al ratio, the anions, and cation substitution. The presence of the sodium carbonate materially enhances the rate of filtration; the absence of sodium carbonate results in a mud which is very difficult to filter.

The rate of metal ion aodition to the aqueous caustic/carbonate solution is not very critical nor is the reaction temperature. The rate of addition can be varied widely. The important feature is an adequate mixing of the metal ion solution and the caustic-carbonate solution. In the absence of efficient agitation, undesired reactions occur which do not lead to a useful product. The addition temperature is best kept at below 100° C.

This results in a slurry of magnesium-aluminum hydroxide which is essentially amorphous to X-rays. Only after a suitable heat aging or crystallization do these filtered and dried solids have a well defined X-ray powder pattern. This crystallization process is an important part of this catalyst preparation. When the crystallization temperature is too low (less than 50°), the rate of crystal formation is so slow as to be impractical. At elevated temperatures the crystal growth is very rapid and may yield too large a crystal (greater than 200°/18 hr). It is best to choose an intermediate temperature of about 65°-75°/18 hr. This yields a crystal of about 150-300 A in size which has a surface area of 100-120 $m^2/g$ (BET/$N_2$ technique).

The subsequent heat treatment is very important. This may be carried out between 300° and 500° C. in air or an inert gas stream or even under vacuum. The heating temperature is very critical. At or below 300° C. the hydrotalcite decomposition process is slow and incomplete. Above 600° C. the resulting metal oxide mixture begins to sinter and lose surface area, pore volume, as well as form a catalytically inactive phase (spinel-$MgAl_2O_4$). The temperature range of 400°-450° C. appears to maximize the catalyst's surface area and the pore volume and drives the reaction to completion in a reasonable period of time (18 hrs).

At this point the fine powder can be pelleted or extruded to form particles which are wear and impact resistant and can function effectively in fixed-bed catalytic converters. Usually some graphite (less than 2%) is added to aid the forming process.

In order for this heat-treated material to be an active and effective catalyst, it is necessary that the interstitial anion conforms to certain criteria. On heating to 350°500° C. the anion must:

Decompose to form a volatile gas leaving behind a hydroxyl group:

$$H_2O + (CO_3^=) \rightarrow 2OH^- + CO_2$$

$$H_2O + 2NO_3^- \rightarrow 2OH^- + 2NO_2 + 0.5O_2$$

Decompose to form an inert metal oxide and a hydroxyl group:

$$H_2O + Cr_2O_7^= \rightarrow Cr_2O_3 + 1.5O_2 + 2OH^-$$

In the event that the interstitial anion cannot decompose in this manner at less than 500° C., then the resulting heated material will be substantially inactive as a catalyst. The reason for this is that the anions remain intact and cannot generate the catalytically needed hydroxyl group. Thus $SO_4^=$, $PO_4^=$, $ClO_4^-$, $BO_3^=$, $F^-$, $Cl^-$, $Br^-$, and $I^-$ do not decompose or volatilize under these circumstances, hence the heated material lacks catalyst activity.

Particularly desirable interstitial anions appear to be the long chain aliphatic alpha-omega dicarboxylates such as adipic, decane, and dodecane dicarboxylates. These appear to function in a dual manner:

These large anions expand the space between the metal hydroxide sheets from about 3-5 Å to about 20 Å.

On oxidative burn-off, the volume of hydrocarbon to be burned to $CO_2$ and $H_2O$ is such that it expands the lattice even more, thereby resulting in catalysts which have unusually high surface areas (about 250 $m^2/g$) and pore volumes (about 1 cc/g).

This results in very active catalytic materials.

While acetone is the preferred active hydrogen containing organic carbonyl substrate used with these hydrotalcite catalysts, because of the commercial importance of its aldol condensation products, i.e., isophorone and mesityl oxide, other substrates readily undergo aldol condensation over these catalysts. Other exemplary substrates are presented below.

The preferred temperature for converting acetone to mesityl oxide and isophorone using the catalysts of this invention lies in the range of about 250° to about 350° C. with a more preferred range lying in the range of about 280° to about 320° C.

Pressure is not narrowly critical but pressures of about 1 to about 5 atmospheres are preferred. If desired the conversion of acetone with the catalysts of this invention can be effected at atmospheric and below as well as higher atmospheric pressures.

The feed rate of acetone is not narrowly critical but it is preferred for efficient operations to range between about 20 and 140 pounds of acetone per/hour/foot$^3$ of catalyst. This corresponds to an hourly vapor space velocity of about 90 to about 700 cubic feet of gaseous acetone per cubic foot of catalyst per hour. At about 300° C. and 3 atmospheres, the preferred contact time is about 5 to about 40 seconds.

It is preferred to hold percent conversion of acetone in the range of about 7 to about 40 percent by weight.

The life of the catalysts of this invention is surprisingly long and is in excess of about 25,000 hours for the efficient conversion of acetone. An unexpected attribute of these catalysts is the fact that their life can be extended further by regeneration consisting of heating the catalyst in the presence of air or oxygen at a temperature in the range of about 250° C. to 450° C. thereby burning off any adhering polymer and non-volatile by-products. Surprisingly the regenerated catalyst is as active and efficient and in many cases more active and efficient than the original catalyst.

The terms conversion and efficiency of the acetone conversion are used in this invention as defined below:

Conversion = $10^2 \times (B/A)$

Efficiency = $10^2 \times (MSO+I)/B$

Where:

A = Total Acetone equivalents fed
B = Total Acetone equivalents in product(s)
MSO = Total equivalents of acetone in the mesityl oxide product
I = Total equivalents of acetone in isophorone product.

The term "Acetone Equivalent" is one for acetone, two for mesityl oxide and three for isophorone for purposes of this disclosure. It simply accounts for each mole of acetone fed passing through to the reactor whether in reacted or unreacted form.

While the highest rates and efficiencies are obtained by using an anhydrous acetone feed having a purity of 99 percent or greater, this invention can be used with acetone having a purity as low as about 70 percent by weight with the balance being mesityl oxide, water and other materials, such as, isopropanol, hexenes, and the like.

The conversion of acetone to mesityl oxide and isophorone according to this invention is preferably carried out over a fixed catalyst bed.

The catalysts of this invention do not require a support. They can be pelleted, extruded or shaped into any desired form. However, if desired they can also be formulated to be carried on an inert material.

The testing of these catalyst compositions was carried out by two methods. The first involved the use of a pulse reactor-gas chromatographic combination which yields rapid and semi-quantitative data. This was used principally as a screening tool to detect highly active catalysts for subsequent testing. Also the reaction chemistry and other features were examined by this technique. The second method was a one-inch i.d. pilot plant reactor. In this latter device, long-term testing was carried out.

The initial screening operations used in the discovery of this catalyst system were effected by means of a pulse reactor consisting of a modified Hewlett-Packard Model 5750-B gas chromatograph. The gas chromatograph separation column was 10 feet long and $\frac{1}{8}$" in diameter packed with 20 percent Carbowax 20 M (Trademark of Union Carbide Corporation for polyethylene glycol having a formula molecular weight range of about 18,000) on Chromosorb T (a polytetrafluoroethylene support sold by Johns-Manville Co.)

The programming schedule was 70° to 210° C. at 8°/min. Detection was by fid (flame ionization detection) although the less sensitive to (thermal conductivity) mode can also be used. The detector temperature was 300° C. Peak integration was carried out electronically.

The injection port kept at 300° C. was $\frac{1}{4}$ inch i.d. into which a 2 mm o.d. glass liner filled with catalyst (about 0.05 g.) was inserted. Specially cut silicone rubber septa prevented gases from by-passing this glass catalyst holder.

In the general procedure six 25 microliter fractions of acetone were initially injected into the catalyst bed. These injections were carried out in rapid succession; after this the catalyst and the separation column was cleared of all reaction products by sweeping helium through for about 2 hours. After these 2 microliter injections of acetone were used to measure the initial catalyst activity.

The pilot plant reactor is described below:

ONE-INCH PILOT PLANT REACTOR

This device consists of a 1" i.d. pipe (300 cm long) made of 304 stainless steel. The bottom 165 cm contained about 1 liter of catalyst. A $\frac{1}{4}$" thermocouple well went through the center of this catalyst bed. In it were 6 thermocouples, equally spaced. Readings were on a multipoint recorder. On each end of the catalyst bed was a glass wool plug (7 cm) and a Carpenter "Neva-Clog" screen. Before the catalyst bed was a 120 cm preheat section of $\frac{1}{4}$" glass balls. Liquid acetone was pumped with a reciprocating plunger pump into a tubular heat exchanger (2 ft.² surface area, steam heated 190 psi) and then directly onto the glass bead section. Vapor flow was in a downward direction. Heating was by $\frac{3}{4}$"-high temperature glass fiber insulated tapes which were controlled by temperature controllers. The reactor pressure was controlled with appropriate valves. Following this was a 2 ft² heat exchanger. Weights (in and out) were on 100 kg. balances (±25 g.). Usually the material balance was within 2%. Gas formation - invariably nil-could be checked with a wet test meter.

Data from this pilot plant reactor can be quantitatively related to plant scale operations.

ANALYTICAL METHODS

Water was determined by Karl Fischer titration or by using thermal conductivity detection. The reactor crudes were analyzed by gas chromatography. Area-wt. % correlations were established using synthetic known samples.

Typical pulse-reactor results are presented later. They were calculated from the pulse reactor-gas chromatographic runs carried out by the above procedure. Calcium hydroxide, a commonly used heterogeneous catalyst for acetone aldol condensations, was added as a reference but was relatively inactive.

The activity of each catalyst can be inferred from the recovered acetone percentage. The smaller this number the more acetone is converted, the more active the catalyst is.

The term "active hydrogen-containing organic compounds" as used herein includes those having the group

adjacent to a aldehydic or ketonic carbohyl group, a nitro group, a cyano group and other electron withdrawing groups such as those present in quaternary salts.

Preferred active hydrogen containing organic carbonyl compounds which are susceptible to aldol condensation using the catalysts of this invention include aliphatic aldenydes, such as, formaldehyde in conjunction with other active hydrogen containing compounds, acetaldehyde, n-butyraldehyde and the like; aliphatic ketones such as methyl ethyl ketone, methyl isobutyl ketone, diethyl ketone, and the like; cycloaliphatic ketones, such as, cyclohexanone, as well as acetone.

The above described catalysts unexpectedly demonstrate selective reactivity even for such closely related aliphatic aldehydes as n-butyraldehyde and its isomer isobutyraldehyde. It was demonstrated that n-butyraldehyde reacted over 8 times faster than isobutyraldehyde in an aldol condensation using these catalysts.

The invention is further described in the examples which follow. All parts and percentages are by weight unless otnerwise specified.

EXAMPLE 1

Preparation of Mg-Al-CO$_3$ Hydrotalcite Catalyst

A 5-liter, 4-necked round bottomed flask was equipped with an addition funnel, mechanical stirrer, reflux condenser, and thermometer. It was nitrogen purged and a solution of 480 g 50% aqueous NaOH (6.0 mole) and 100 g NaCO$_3$ was added to 2000 ml distilled water. To this was added a solution of 384 g Mg(NO$_3$)$_2$.6H$_2$O(1.50 mole) and Al$_2$(NO$_3$)$_3$.9H$_2$O(1.00 mole) in 1600 ml distilled water over a 2-hour period with good mechnical agitation. There was a slight exotherm and a white, milky ppt. appeared at once. At the end the slurry was not very thick. The temperature was then adjusted to 65° C. and kept there for 18 hours. After cooling the slurry was filtered, the solid washed twice with distilled water, and dried 125° C./vac/18 hours. This results in about 170 g of a white hard solid. The X-ray powder patterns showed a very well developed hydrotalcite pattern (ASTM D-22-700). The peaks are relatively broad which can be attributed to the small crystal size (about 150 A). A typical analysis is shown below:

| Component | Found (Wt. %) |
|---|---|
| Ash | 57.39 |
| Mg (on ashed sample) | 35.34 |
| Al (on ashed sample) | 17.72 |
| Na | 0.0058 |
| N | 0.012 |
| C | 2.50 |
| Mg/Al ratio | 2.24 |

Heat treatment was carried out in a muffle furnace at 450° C. in air for 18 hours.

EXAMPLES 2-7

In order to demonstrate the use of the calcined synthetic hydrotalcite of this invention as a catalyst not only for the condensation of acetone but as a general aldol condensation catalyst, the following compounds were also used as substrates in place of acetone: methylisobutylketone, cyclohexanone, acetaldehyde, a mixture of acetaldehyde and benzaldehyde, and butyraldehyde.

The pulse reactor described above was employed for those experiments at 300° C. using 0.050 g of 50/80 mesh, heat activated synthetic hydrotalcite catalyst prepared as described above. The catalyst had a Mg/Al ratio of approximately 2.6 and a BET[S. Brunauer, P. H. Emmett and E. Teller, J. Amer. Chem. Soc., 60, 309 (1938)]surface area of 155 meters$^2$/g. The catalyst was further activated with 150 microliters of acetone (300° C. and 60 psig of helium). In each run 2 microliters of the substrate was injected into the pulse reactor. The products were analyzed by gas phase chromatography using the area % of each product as an indication of the relative yields of products of each run.

As a standard for comparison, acetone was run first, the effluent from the reactor contained 45% acetone, 2.1% mesityl oxide oxide 2% unknown mid-range products, 36.2% isophorone, 7.5% isoxylitones and 6.6% tetralone.

Methylisobutylketone yielded 73.3% methyisobutylketone, 16.5% diisobutyl ketone and unknown mid-range products of 4.3% and 1.3% and high boilers of 2.7% and 1.1%.

Cyclohexanone produced an effluent containing 58.5% cyclohexanone, 1.8% and 1.6% of mid-range unknowns, 23.9% and 12.9% respectively of products having the structures

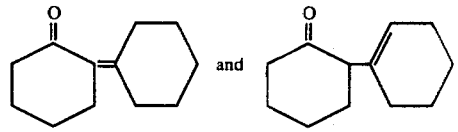

Acetaldehyde afforded an effluent containing 19.7% acetaldehyde, 21.4% of dialdehydes, 34.1% of C$_6$ aldehydes and unknowns of 2.1%, 4.0%, 2.7%, 6.8% and 1.4%.

A mixture of acetaldehyde (0.5 ml) and benzaldehyde (1.5 ml) yielded an effluent containing 0.7% acetaldehyde, 89.4% benzaldehyde, 3.8% of unknowns and 3.3% of an aldehyde having the structure $$C_6H_5CH{=}CH{-}\overset{\overset{\displaystyle O}{\|}}{C}H$$

Butyraldehyde yielded an effluent containing 47.2% unreacted butyraldehyde, 36.6% C$_8$ aidehyde and the remainder were six unknown fractions.

EXAMPLES 8-12 a-d

Several compounds have been prepared in which substitutions of ions have been made in the hydrotalcite structure:

$$(M^{+2})_6(M^{+3})_2(OH)_{16}(X^-)_2.4H_2O$$

wherein M$^{+2}$ is Mg$^{++}$, M$^{+3}$ is Al$^{+3}$ and (X$^-$) is CO$_3$ in the synthetic hydrotalcite catalyst of this invention. However, this invention also covers hydrotalcite related structures where M$^{+2}$ is Zn, Ni, Co, Cr, or Ni/Mg mixtures in place of Mg. These were tested for catalytic activity in the condensation of acetone. The results are shown in Table 1 compared with the original hydrotalcite containing Mg.

These data demonstrate that an isomorphous replacement of the divalent cation in the hydrotalcite lattice does not materially affect tne catalytic effect of the resultant catalyst for the aldol condensation of acetone.

EXAMPLE 13-15

Similarly the replacement of Al$^{+3}$ in the original hydrotalcite by Fe$^{+3}$ and Cr$^{+3}$ yielded hydrotalcites which were catalytically active for the aldol condensation of acetone. As shown in Table 2, the activity of the Fe$^{+3}$ containing catalyst was virtually identical to that of the Al$^{+3}$ isomorph. The Cr$^{+3}$ containing catalyst became highly active only on heat treatment at 400° C.

The replacement of $Al^{+3}$ by a mixture of $Al^{+3}$ and $Cr^{+3}$ also afforded active aldol condensation catalysts.

EXAMPLES 16-21

The data in Table 3 illustrate that hydrotalcites can be synthesized in which the Mg/Al ratio varies between 1.38 and 6.27.

TABLE 1
EFFECT OF ISOMORPHOUS SUBSTITUTION OF $M^{+2}$ IN THE HYDROTALCITE LATTICE ON CATALYTIC ACTIVITY

| | Example[a] | | | | | | | |
|---|---|---|---|---|---|---|---|---|
| | 8 | 9 | 10 | 11 | 12a | 12b | 12c | 12d |
| $M^{+2}$ | Mg | Zn | Zn | Ni | Co | Ni + Mg | Mg | Zu |
| $M^{+3}$ | Al | Al | Al | Al | Al | Al | Al + Cr | Cr |
| $M^{+2}/M^{+3}$ | | | | | | | | |
| Charged | 2.00 | 2.00 | 2.00 | 2.00 | 2.00 | 3.00 | 3.00 | 3.00 |
| Product Analysis | 2.24 | 2.66 | 2.66 | 2.07 | 2.16 | 2.87 | 2.45 | 3.03 |
| X-ray[b] | HT | HT | HT | HT[c] | HT[c] | HT | HT | HT |
| Carbon Theory (%) | 1.81 | 1.32 | 1.32 | 1.38 | 1.38 | 1.70 | — | 1.33 |
| Carbon Found (%) | 2.50 | 1.32 | 1.54 | 1.71 | 1.78 | 2.22 | 2.21 | 2.45 |
| Pulse Reactor Catalytic Activity | | | | | | | | |
| Acetone Conv. (%) | 24.6 | 12.5 | 10.5 | 34 | 22.8 | 37 | 30 | 11.1 |
| Conv. Eff. (%) | 76.3 | 86 | 94 | 66 | 91.4 | — | — | 99.7 |

[a]All preparations were carried out as per Example 1 except Example 10. In this preparation the metal nitrate and caustic-carbonate solutions were added at equal rates to a well-stirred reactor. Subsequent treatments were unchanged.
[b]HT—hydrotalcite.
[c]Strong fluorescence.

TABLE 2
EFFECT OF ISOMORPHOUS SUBSTITUTION OF $M^{+3}$ IN THE HYDROTALCITE LATTICE

| | Example[a] | | |
|---|---|---|---|
| | 13 | 14 | 15 |
| $M^{+3}$ | Al | Cr | Fe |
| $M^{+2}$ | Mg | Mg | Mg |
| $M^{+2}/M^{+3}$ | | | |
| Charged | 2.00 | 2.00 | 2.00 |
| Product Analysis | 2.24 | 1.88 | 2.11 |
| X-ray[b] | HT | HT[c] | HT[c] |
| Carbon Theory (%) | 1.81 | 1.62 | 1.60 |
| Carbon Found (%) | 2.50 | 1.64 | 1.72 |
| Pulse Reactor Catalytic Activity | | | |
| Acetone Conv. (%) | 24.6 | 23.2 | 26.5 |
| Conv. Eff. (%) | 76.3 | 86.0 | 80.5 |

[a]Preparations were carried out as per Example 1.
[b]HT = hydrotalcite.
[c]Strong Fluoresence.

TABLE 3
EFFECT OF VARIATION OF HYDROTALCITE Mg/AL RATIO ON CATALYTIC ACTIVITY

| | Example[a] | | | | | |
|---|---|---|---|---|---|---|
| | 16 | 17 | 18 | 19 | 20 | 21 |
| $Mg^{+2}/Al^{+3}$ | | | | | | |
| Charged | 1.00 | 1.33 | 2.00 | 2.50 | 3.03 | 5.0 |
| Product | 1.39 | NA | 2.24 | 2.27 | 3.04 | 6.27 |
| X-ray[b] | HT+ | HT | HT | HT[d] | HT[e] | HT[d] |
| Carbon Theory (%) | — | — | 1.81 | 1.81 | 1.99 | — |
| Carbon Found (%) | 2.22 | NA | 2.50 | 2.25 | 2.36 | 1.42 |
| Pulse Reactor Catalytic Activity | | | | | | |
| Acetone Conv. (%) | 37.5 | 21.0 | 24.6 | 15.0 | 22.5 | 24.2 |
| Conv. Eff. (%) | 83.8 | 85.6 | 76.3 | 88.9 | 81.0 | 91.1 |

[a]Preparations were carried out as per Example 1 except that the Mg—Al ratios were varied.
[b]HT = hydrotalcite.
[c]Includes a trace of hydromagnesite $Mg_2(OH)_2(OH)_2CO_3$.
[d]Plus $Al(OH)_3$ Bayerite, Gibsite, and Norstrandite.

TABLE 4
EFFECT OF ISOMORPHOUS REPLACEMENT OF INTERSTITIAL ANIONS

| | Example[a] | | | | | | | | | |
|---|---|---|---|---|---|---|---|---|---|---|
| | 22 | 23 | 24 | 25 | 26 | 27 | 28 | 29 | 30 | 31 |
| Preparative Conditions | Metal $SO_4^=$ w/o $CO_3^=$ | Metal $SO_4^=$ w $CO_3^=$ | Metal $Cl^-$ w/o $CO_3^=$ | Metal $Cl^-$ w $CO_3^=$ | Metal $NO_3^-$ w/o $CO_3^=$ | Metal $NO_3^-$ w/o $CO_3^=$ | Metal $NO_3^-$ w $NO_3^-$ excess | Metal $NO_3^-$ w $OAc^-$ | Metal $NO_3^-$ w $n$-$C_4H_9CO_2^-$ | Metal $NO_3^-$ w oxalate |
| Filtration Characteristics | poor weak Ht | good HT | very poor HT | good HT | very poor HT | good HT | poor HT | poor HT | fair diffuse HT | fair HT |
| X-ray[b] | "MgAlOHSO$_4$"[c] | | | | | | | | | |
| Mg/Al Charged | 1.88 | 1.88 | 2.00 | 2.00 | 2.00 | 2.00 | 3.33 | 2.00 | 2.00 | 2.00 |
| Mg/Al Product | 2.50 | 2.05 | 2.32 | 2.01 | 2.56 | 2.24 | 3.50 | 2.57 | 1.97 | 2.92 |
| Analyses (%) | | | | | | | | | | |
| S | 4.73 | .00 | — | — | — | — | — | — | — | — |
| Cl | — | — | 5.38 | .00 | — | — | — | — | — | — |
| N | — | — | — | — | .77 | .12 | 2.01 | 1.47 | 1.60 | .04 |
| C | .63 | 2.40 | 1.22 | 2.41 | .88 | 2.50 | .59 | 0.58 | 13.45 | 4.34 |
| Pulse Reactor Catalytic Activity | | | | | | | | | | |
| Acetone Conv. (%) | 0 | 26 | 10.3 | 35.6 | 19.8 | 24.6 | 17.9 | 24.7 | 44.3 | 32.0 |

TABLE 4-continued
EFFECT OF ISOMORPHOUS REPLACEMENT OF INTERSTITIAL ANIONS

| | Example[a] | | | | | | | | | |
|---|---|---|---|---|---|---|---|---|---|---|
| | 22 | 23 | 24 | 25 | 26 | 27 | 28 | 29 | 30 | 31 |
| Conv. Eff. (%) | — | 78 | 91.9 | 85.6 | 85.5 | 76.3 | 80.5 | 84.7 | 84.1 | 86.0 |

[a]Preparations were carried out as per Example 1 except for appropriate substitutions as indicated.
[b]HT—hydrotalcite.
[c]Presence of Mg—Al hydroxy sulfates.
[d]w = with.
[e]w/o = without.

EXAMPLES 22–31

The interstitial anion or anions are an essential part of the hydrotalcite lattice. In nature normally only the carbonate is found. Synthetic hydrotalcites can be made which contain many other anions in the crystal lattice. However, the standard procedure of Example 1 could not be used when sulfate was substituted for carbonate because the resultant precipitates were thin and difficult to filter and did not crystallize into the hydrotalcite lattice on heating at 65° C.

Table 4 shows the effect of isomorphous replacement of interstitial anions in the hydrotalcite lattice. Divalent anions from dibasic acids having 1 to 12 carbons can be used.

EXAMPLE 32

An evaluation of the $MgO-Al-CO_3$ catalysts (heat treated hydrotalcite) prepared as in Example 1 was carried out in the 1 inch Pilot Plant Reactor described supra using acetone as the substrate 23%. Conversion and 77% efficiency to isophorone and mesityl oxide and other pertinent data are presented in Table 5.

The synthetic hydrotalcites of this invention freshly heat-activated (450° C. in air for 18 hours) show ion exchange activity as inorganic anion exchangers. Above 50 percent exchange or adsorption of fluoride and such multivalent anions as sulfate, sulfite, sulfide, carbonate, phosphate, chromate, oxalate, and acetate took place with this hydrotalcite.

TABLE 5
EVALUATION OF HYDROTALCITE IN 1" REACTOR [1]

| Catalyst | Hydrotalcite ⅛"<br>Tablets<br>(Heated 400°) |
|---|---|
| Run No. | 32 |
| Results | |
| Acetone Conversion (%) | 23.3 |
| Efficiency to MSO + I | 77.7 |
| MSO/I (wt.) | 0.32 |
| Crude Analyses (dry basis, wt. %) | |
| Acetone | 80.7 |
| Mesityl Oxide | 3.70 |
| Isophorone | 11.6 |
| Midrange unknown products | 0.66 |
| Isoxylitones | 0.82 |
| Tetralone | 2.50 |
| Conditions | |
| Feed Rate (g/hr) | 680 |
| Temperature (°) | 300 |
| Pressure (psi) | 40 |
| Time on Stream (hr) | 450 |

[1]Catalyst bed depth 80".

Although the invention has been described in its preferred forms with a certain amount of particularity, it will be understood by those skilled in the art that the present disclosure has been made only by way of example and that numerous changes can be made without departing from the spirit and scope of the invention.

I claim:

1. Method of preparing aldol condensation catalysts which comprises the steps of:
   (1) Adding mixed aqueous solutions of divalent and trivalent inorganic salts to a solution of a stoichiometric amount of sodium hydroxide and sodium carbonate at ambient temperature with vigorous stirring whereby a slurry is obtained;
   (2) Heating the slurry from (1) at about 60°–200° C. until crystallization occurs providing a synthetic anionic clay mineral having the generic formula:

$$M_m N_n (OH)_{(2m+2n)} A_a \cdot b H_2 O$$

wherein
   M is a divalent metal cation;
   N is a trivalent metal cation;
   A is a mono-, di- or trivalent anion which decomposes at about 300°–500° C. to form a volatile gas;
   m and n are such that m/n has values of 1 to about 6;
   a is a number with the provisos that when A is a monovalent anion, a=n, when A is a divalent anion, a=½n, and when A is a trivalent anion a=⅓n, and b is an integer having values of 1 to 10;
   (3) Filtering the solids from the slurry in (2);
   (4) Washing the filtered solids with water;
   (5) Heating the filtered solids from (4) to a temperature of about 300° to about 600° C.; and
   (6) Recovering the heated solids from (5) as an aldol condensation catalyst.

2. Method claimed in claim 1 wherein the synthetic anionic clay mineral has the formula:

$$M_6 N_2 (OH)_{16} A \cdot 4 H_2 O.$$

3. Method claimed in claim 2 wherein M is $Mg^{+2}$ and A is $CO_3^{-2}$.

4. Method claimed in claim 2 wherein M is $Ni^{+2}$, N is $Cr^{+3}$, and A is $CO_3^{-2}$.

5. Method claimed in claim 2 wherein M is a mixture of $Ni^{+2}$ and $Mg^{+2}$, N is $Al^{+3}$ and A is $CO_3^{-2}$.

6. Method claimed in claim 2 wherein M is $Mg^{+2}$, N is a mixture of $Al^{+3}$ and $Cr^{+3}$ and A is $CO_3^{-2}$.

7. Method claimed in claim 2 wherein M is $Zn^{+2}$, N is $Cr^{+3}$ and A is $CO_3^{-2}$.

8. Mineral made by the method claimed in claim 3.
9. Mineral made by the method claimed in claim 4.
10. Mineral made by the method claimed in claim 5.
11. Mineral made by the method claimed in claim 6.
12. Mineral made by the method claimed in claim 7.
13. Method claimed in claim 1 wherein A is a monocarboxylate anion.
14. Method claimed in claim 13 wherein the monocarboxylate anion is an acetate anion.
15. Method claimed in claim 1 wherein A is a nitrate anion.
16. Method claimed in claim 1 wherein A is a polycarboxylate anion.
17. Method claimed in claim 16 wherein the polycarboxylate anion is an oxalate anion.

* * * * *